United States Patent
Shriram et al.

(10) Patent No.: US 11,452,494 B2
(45) Date of Patent: Sep. 27, 2022

(54) METHODS AND SYSTEMS FOR PROJECTION PROFILE ENABLED COMPUTER AIDED DETECTION (CAD)

(71) Applicant: GE Precision Healthcare LLC, Wauwatosa, WI (US)

(72) Inventors: Krishna Seetharam Shriram, Bangalore (IN); Arathi Sreekumari, Bangalore (IN); Rakesh Mullick, Bangalore (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 459 days.

(21) Appl. No.: 16/575,092

(22) Filed: Sep. 18, 2019

(65) Prior Publication Data
US 2021/0077059 A1   Mar. 18, 2021

(51) Int. Cl.
A61B 8/08 (2006.01)
A61B 8/14 (2006.01)
G06T 7/00 (2017.01)

(52) U.S. Cl.
CPC ............ A61B 8/0825 (2013.01); A61B 8/085 (2013.01); A61B 8/14 (2013.01); A61B 8/483 (2013.01);
(Continued)

(58) Field of Classification Search
CPC ......... A61B 8/0825; A61B 8/085; A61B 8/14; A61B 8/483; A61B 8/5223;
(Continued)

(56) References Cited

U.S. PATENT DOCUMENTS

| | | | |
|---|---|---|---|
| 2009/0005679 A1* | 1/2009 | Dala-Krishna | G06T 7/80 600/437 |
| 2020/0098125 A1* | 3/2020 | Langeland | G06T 7/70 |
| 2021/0401407 A1* | 12/2021 | Yang | G06T 7/75 |

OTHER PUBLICATIONS

"Dedicated Computer-Aided Detection Software for Automated 3D Breast Ultrasound; An Efficient Tool for the Radiologist in Supplemental Screening of Women With Dense Breasts", Jan C.M. van Zelst, et al., European Radiology, 2018, 11 pages.
(Continued)

*Primary Examiner* — Vu Le
*Assistant Examiner* — Winta Gebreslassie
(74) *Attorney, Agent, or Firm* — McAndrews, Held & Malloy, Ltd.; Jacob Groethe; David Bates

(57) ABSTRACT

Systems and methods are provided for projection profile enabled computer aided detection (CAD). Volumetric ultrasound dataset may be generated, based on echo ultrasound signals, and based on the volumetric ultrasound dataset, a three-dimensional (3D) ultrasound volume may generated. Selective structure detection may be applied to the three-dimensional (3D) ultrasound volume. The selective structure detection may include generating based on a projection of the three-dimensional (3D) ultrasound volume in a particular spatial direction, a two-dimensional (2D) image; applying two-dimensional (2D) structure detection to the two-dimensional (2D) image, to identify structure candidates associated with a particular type of structures; selecting for each identified structure candidate, a corresponding local volume within the three-dimensional (3D) ultrasound volume; applying three-dimensional (3D) structure detection to each selected local volume; and identifying based on applying the three-dimensional (3D) structure detection, one or more structure candidates that match the particular type of structures.

20 Claims, 9 Drawing Sheets

(52) U.S. Cl.
CPC .......... *A61B 8/5223* (2013.01); *A61B 8/5253* (2013.01); *G06T 7/0012* (2013.01); *G06T 2207/10136* (2013.01); *G06T 2207/20081* (2013.01); *G06T 2207/20084* (2013.01); *G06T 2207/30068* (2013.01); *G06T 2207/30096* (2013.01)

(58) Field of Classification Search
CPC ............ A61B 8/085525; G06T 7/0012; G06T 2207/0136; G06T 2207/20081; G06T 2207/20084; G06T 2207/30068; G06T 2207/30096
See application file for complete search history.

(56) References Cited

OTHER PUBLICATIONS

Tumor Detection in Automated Breast Ultrasound Using 3-D CNN and Prioritized Candidate Aggregation, Tsung-Chen Chiang, et al., IEEE Transactions on Medical Imaging, vol. 38, No. 1, Jan. 2019, 10 pages.

"Densely Deep Supervised Networks with Threshold Loss for Cancer Detection in Automated Breast Ultrasound", Na Wang, et al., Springer Nature Switzerland AG, 2018, 8 pages.

* cited by examiner

METHODS AND SYSTEMS FOR PROJECTION PROFILE ENABLED COMPUTER AIDED DETECTION (CAD)

FIELD

Aspects of the present disclosure relate to medical imaging. More specifically, certain embodiments relate to methods and systems for projection profile enabled computer aided detection (CAD).

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Various issues may exist with existing solutions for detecting particular structures during medical imaging. In this regard, conventional systems and methods, if any existed, for detecting abnormalities (e.g., tumors or lesions) during medical imaging operations, can be inefficient and/or ineffective.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for a projection profile enabled computer aided detection (CAD), substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
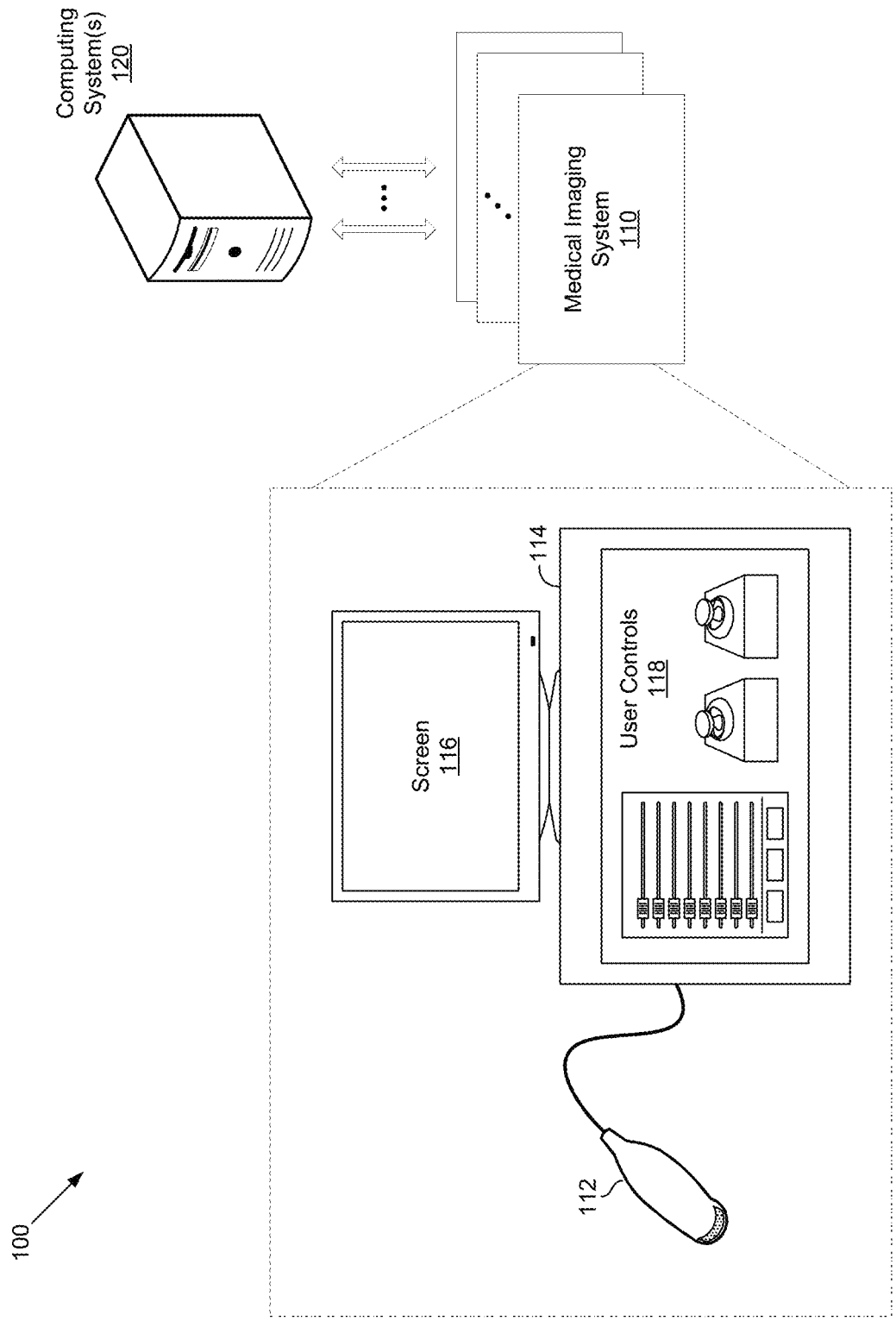
FIG. 1 is a block diagram illustrating an example medical imaging arrangement that supports projection profile enabled computer aided detection (CAD), in accordance with the present disclosure.

Certain implementations in accordance with the present disclosure may be directed to ultrasound imaging with projection profile enabled computer aided detection (CAD). In particular, various embodiments have the technical effect of enhancing detection of abnormalities (e.g., tumors or lesions) during medical imaging operations, and particular doing in optimal manner—e.g., reducing computational requirement for such detection. This may be done, for example, by obtaining three-dimensional (3D) volumes of the scanned area, using optimized two-dimensional (2D) detection techniques (e.g., using learning algorithms) to identify candidate regions in two-dimensional (2D) images generated based on the 3D volume, and then identify local volumes corresponding to the identified candidates, and then apply optimized two-dimensional (2D) detection techniques to these local volumes. Aspects of the present disclosure have the technical effect of allowing for the benefits of 3D detection without the computation requirement of performing 3D detection whole 3D volumes; rather, limiting it to regions associated with candidate abnormalities.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIGS. 1 and 2.

Figure 2:
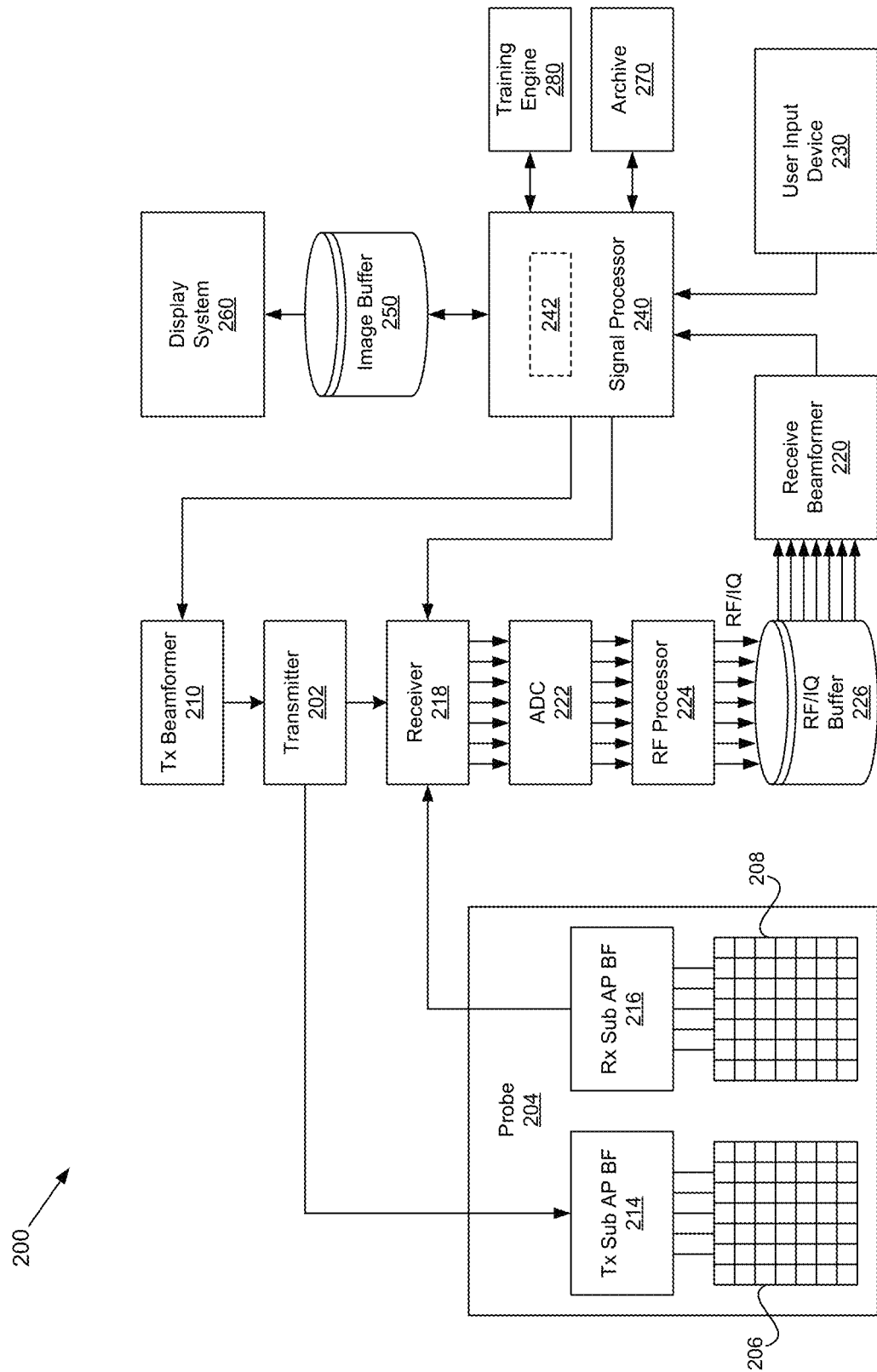
FIG. 2 is a block diagram illustrating an example ultrasound that supports projection profile enabled computer aided detection (CAD), in accordance with the present disclosure.

FIG. 1 is a block diagram illustrating an example medical imaging arrangement that supports projection profile enabled computer aided detection (CAD), in accordance with the present disclosure. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system, which may correspond to the medical imaging system 110, is described in more detail with respect to FIG. 2.

As shown in FIG. 1, the medical imaging system 110 may comprise a probe 112, which may be portable and movable, and a display/control unit 114. The probe 112 may be configured for generating and/or capturing particular type of signals (or data corresponding thereto), such as by being moved over a patient's body (or part thereof). For example, where the medical imaging system 110 is an ultrasound system, the probe 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost (by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110.

In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other Cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In various implementations, the medical imaging system 110 may support projection profile enabled computer aided detection (CAD), as described below.

FIG. 2 is a block diagram illustrating an example ultrasound that supports projection profile enabled computer aided detection (CAD), in accordance with the present disclosure. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1 in ultrasound imaging use scenarios.

As shown in FIG. 2, the ultrasound system 200 comprises, for example, a transmitter 202, an ultrasound probe 204, a transmit beamformer 210, a receiver 218, a receive beamformer 220, a RF processor 224, a RF/IQ buffer 226, a user input device 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270. The user input device 230 may include button(s), rotary encoder (s), a touchscreen, motion tracking, voice recognition, a mouse device, keyboard, camera and/or any other device capable of receiving a user directive. In certain embodiments, one or more of the user input devices 230 may be integrated into other components, such as the display system 260 or the ultrasound probe 204, for example. As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. Additionally and/or alternatively, the user input device 230 may include image analysis processing to identify probe gestures by analyzing acquired image data.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a structure detection module 242, which comprises suitable circuitry, interfaces, logic, and/or code that may be configured to perform and/or support structure detection, particularly in support of profile enabled computer aided detection (CAD), as described below.

The structure detection module 242 may be configured to, for example, implement and/or use deep learning techniques and/or algorithms, such as using deep neural networks (e.g., a convolutional neural network), and/or may utilize any suitable form of artificial intelligence image analysis techniques or machine learning processing functionality configured to analyze acquired ultrasound images to identify, segment, label, and track structures meeting particular criteria and/or having particular characteristics. The structure detection module 242 may be configured for utilizing these techniques and/or capabilities in facilitating or supporting abnormalities (e.g., lesions) structures in particular body parts (e.g., breasts).

In an example implementation, the structure detection module 242 may be provided as a deep neural network that may be made up of, for example, an input layer, an output layer, and one or more hidden layers in between the input and output layers. Each of the layers may be made up of a plurality of processing nodes that may be referred to as neurons. For example, the structure detection module 242 may include an input layer having a neuron for each pixel or a group of pixels from a scan plane of an anatomical structure. The output layer may have a neuron corresponding to a plurality of pre-defined structures or types of structures. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the structure detection module 242 deep neural network (e.g., convolutional neural network) may identify biological and/or artificial structures in ultrasound image data with a high degree of probability.

In certain embodiments, the structure detection module 242 may be configured to perform or otherwise control at least some of the functions performed thereby based on a user instruction via the user input device 230. For example, the structure detection module 242 may be configured to interact with a user via the user input device 230 to receive instructions for searching the ultrasound image. As an example, a user may provide a voice command, probe gesture, button depression, or the like that instructs the structure detection module 242 to search for a particular structure and/or to search a particular region of the ultrasound image.

The training engine 280 may comprise suitable circuitry, interfaces, logic, and/or code that may be operable to train the neurons of the deep neural network(s) of the structure detection module 242. For example, the structure detection module 242 may be trained to identify particular structures or types of structures provided in an ultrasound scan plane. For example, the training engine 280 may train the deep neural networks of the structure detection module 242 using databases(s) of classified ultrasound images of various structures.

As an example, the structure detection module 242 may be trained by the training engine 280 with ultrasound images of particular structures to train the structure detection module 242 with respect to the characteristics of the particular structure, such as the appearance of structure edges, the appearance of structure shapes based on the edges, the positions of the shapes relative to landmarks in the ultrasound image data, and the like. In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception. For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support projection profile enabled computer aided detection (CAD). In this regard, detection of particular structures (e.g., those corresponding to abnormalities, such as lesions or other tumor-related tissue), particularly in conjunction with certain types of ultrasound scans (e.g., breast related ultrasound scans, may be challenges, and as such it optimizing such detection is desirable. For example, use of automated breast ultrasound screening (ABUS) scans is increasing as an alternative to, and/or in conjunction with other types of breast scanning techniques (e.g., mammography). However, detection of lesion or other suspicious structures during ABUS scan may be challenging. In this regard, during ABUS scans clinicians may have to sift through hundreds of slices to detect and characterize tumors/lesions. Solutions based on the present disclosure allow for enhancing lesions (or other abnormalities) detection during such scans. This may be done, in particular, by incorporate use of deep learning (DL) based approaches to automate at least a portion of the detection functions.

However, DL based processes are computationally expensive when performed on large datasets, as would be the case with 3D scans, and reducing the size the datasets by convention means (e.g., down-sampling) may adversely affect the outcome of the detection as information that would otherwise be used in detecting such structures may be lost or altered.

Accordingly, in implementations according to the present disclosure, an alternative approach may be used, whereby 2D images are obtained based on 3D volumes—e.g., by use of a projection of the imaging data, to effectively collapse a 3D volume onto 2D image. A two-dimensional (2D) detection (e.g., deep learning (DL) based detection) is then applied to identify potential particular structure candidate (e.g., lesion candidates) in the projection images. Once these candidates are identified, a three-dimensional (3D) detection (e.g., deep learning (DL) based detection) may then be performed, at full resolution but in a small portion of the full 3D volume—e.g., being limited to small local neighborhoods of the identified candidates (in the direction of projections). Running 3D detection in full spatial resolution would ensure high specificity and sensitivity for the CAD algorithm. In addition, 3D DL based algorithms run in small local neighborhoods will ensure reasonable speed of operation. In some implementations, additional measures may be incorporated to achieve higher specificity and/or reliability (e.g., validating identified lesions). This may be done, for example, by comparing projections taken along multiple directions and/or by comparing different volumes of the same scanned area (particularly overlapped regions), with true lesions being reinforced and false alarms rejected. Example implementations are described in more details below.

Nonetheless, while various implementations are described with respect particular types of scans (e.g., ABUS scans), the disclosure is not so limited, and the same solutions described herein may be similarly applied to other suitable types of scans.

Figure 3:
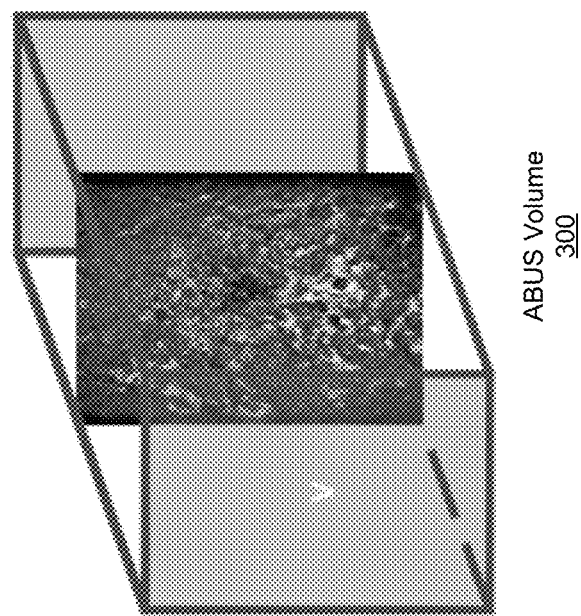
FIG. 3 illustrates an example automated breast ultrasound screening (ABUS) scan that may be processed using projection profile enabled computer aided detection (CAD), in accordance with the present disclosure.
Figure 3:
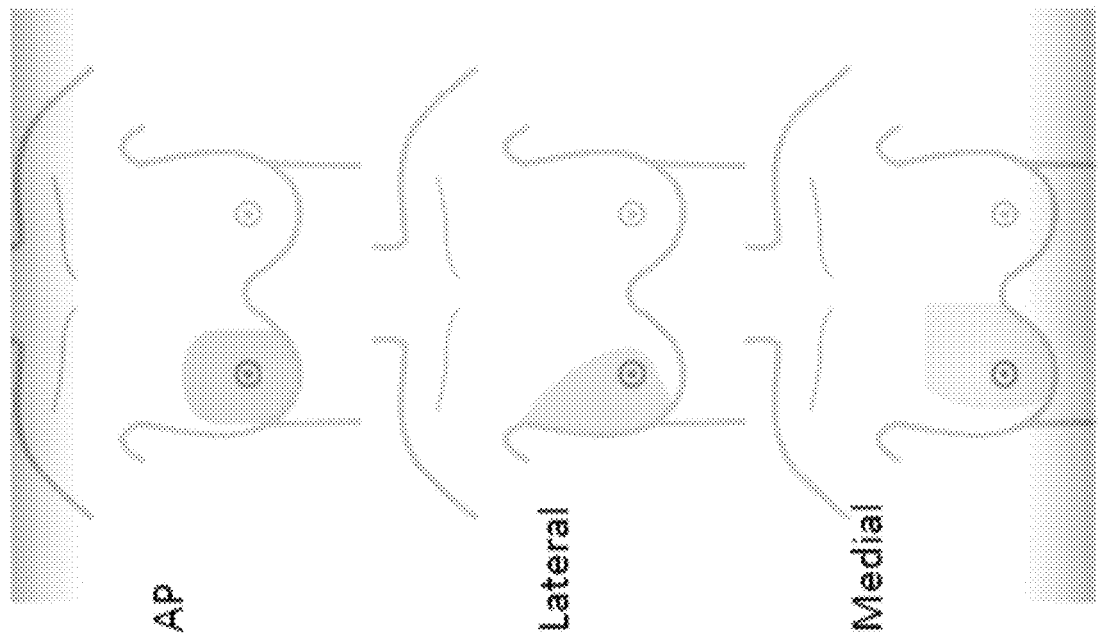

FIG. 3 illustrates an example automated breast ultrasound screening (ABUS) scan that may be processed using projection profile enabled computer aided detection (CAD), in accordance with the present disclosure.

Shown in FIG. 3 is an example three-dimensional (3D) automated breast ultrasound screening (ABUS) volume 300, which may be generated and processed using an ultrasound system, such as the ultrasound system 200 of FIG. 2. In this regard, the ABUS 300 may be generated during automated breast ultrasound screening (ABUS) scan. With such scans, volumetric data may be generated in different directions or orientation relative to the body part being scanned—e.g., with Anteroposterior (AP), Medial and Lateral volumes, corresponding to the Anteroposterior (AP), Medial and Lateral sections of a scanned breast, generated for every scan (as shown in FIG. 3 during an example ABUS scan).

In an example implementation, the size of each ABUS volume may be 843×546×354 voxels, with each voxel having dimensions of 0.2×0.073×1 mm. The objective of such ABUS scans is to detect for abnormalities (e.g., lesions), which may correspond to tumors. However, applying lesion detection to 3D volumes may have many disadvantageous.

In this regard, lesion detection may be better suited for adaptive identification techniques, such as by use of deep learning (DL) type approaches. For best results, DL based detection has to be done on three-dimensional (3D) volumes. Performing deep learning (DL) based detection on 3D volumes may be computationally extensive. Given the computational complexity, the ABUS volume maybe processed to reduce computation complexity, such as by down-sampling the 3D volume during the detection process. This may lead to loss of information, however, especially around smaller lesions. Alternatively, deep learning (DL) detection may be run on rasterized 3D patches of the ABUS volume for lesion detection. However, given the size of the volume, too many locations have to be polled for detection, slowing down the detection process.

Implementations in accordance with the present disclosure may address some of these disadvantageous. In particular, various example implementations may incorporate use of smarter down selection to avoid (e.g., eliminate) 'normal' locations—that is, regions with no abnormalities, such that 3D DL detection may be focused on only 'interesting' regions—that is, regions with possible abnormalities (e.g., lesions). In other words, implementations in accordance with the present disclosure may allow for, and incorporate localized lesion detection (e.g., DL based detection) of only 'interesting' 3D regions in the ABUS volume. Thus, vast amount of data may be first consolidated. This may be done, for example, by taking two-dimensional (2D) projections of the ABUS volume, which may be processed as 2D images for purposes of detection of any abnormalities. In other words, by taking a projection in a particular direction, the volume is collapsed into a two-dimensional (2D) image, with possible abnormalities (e.g., lesions) appearing as intensity troughs. This is illustrated in FIG. 4.

Figure 4:
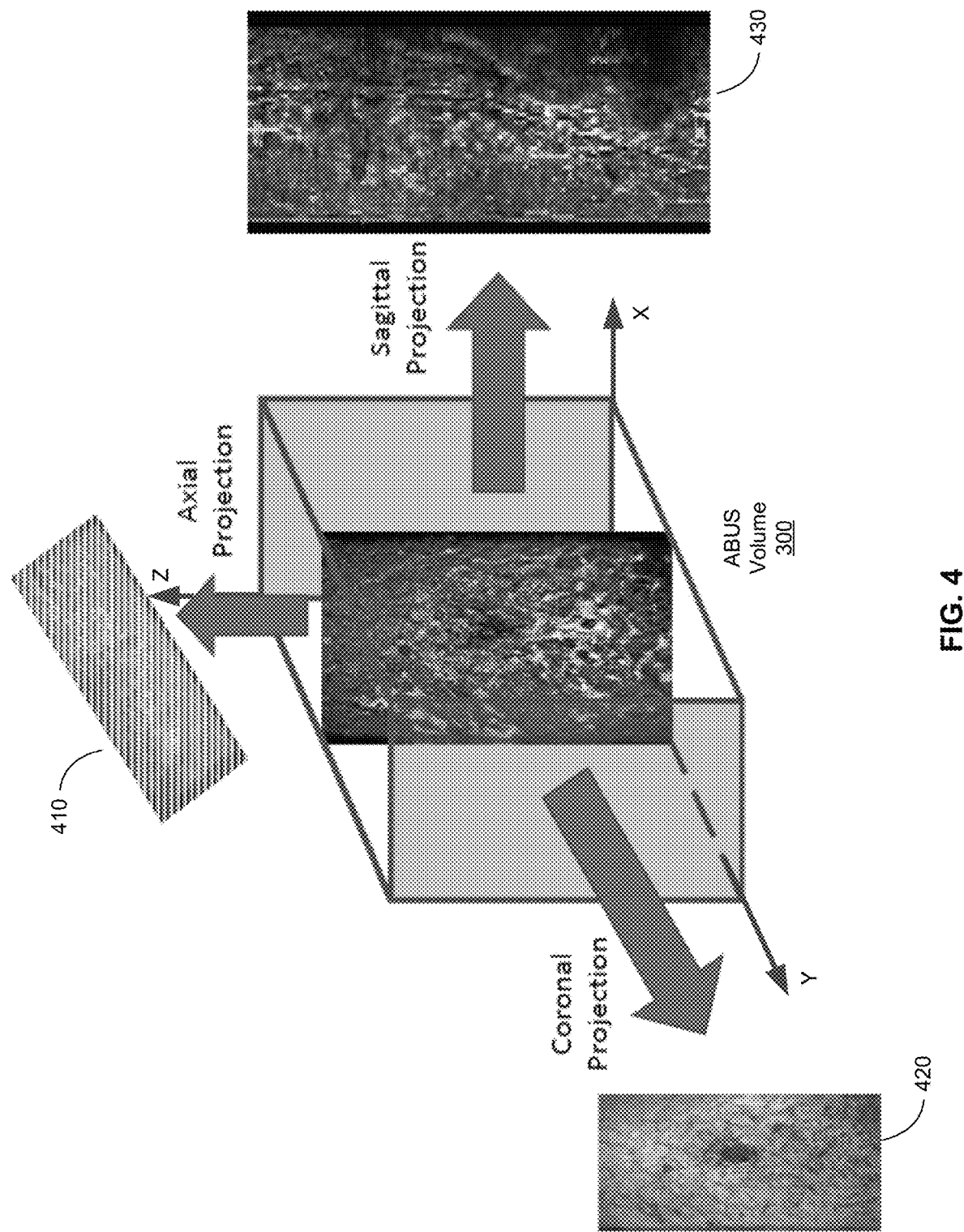
FIG. 4 illustrates an example projection based consolidation of automated breast ultrasound screening (ABUS) volume, in accordance with the present disclosure.

FIG. 4 illustrates an example projection based consolidation of automated breast ultrasound screening (ABUS) volume, in accordance with the present disclosure. Shown in FIG. 4 is an example projection based consolidation of the ABUS volume 300 described with respect to FIG. 3.

In this regard, a number of two-dimensional (2D) images may be generated based on projections of the ABUS volume 300 in different directions. Particularly, as illustrated in FIG. 3, using the x-, y-, and z-axis, three projections may be used to generated three corresponding 2D images based on the ABUS volume 300: axial 2D image 410 corresponding to an axial projection of the ABUS volume 300—that is, in the direction of the z-axis (or z-direction); coronal 2D image 410 corresponding to an coronal projection of the ABUS volume 300—that is, in the direction of the y-axis (or y-direction); and sagittal 2D image 410 corresponding to an sagittal projection of the ABUS volume 300—that is, in the direction of the x-axis (or x-direction).

Once generated, the 2D images may be used for enhanced detection in accordance with the present disclosure. In this regard, each of the projection-based 2D images may be processed for detecting regions therein corresponding to candidate abnormalities (e.g., legion). Then, selective 3D detection may be applied only to these identified regions (e.g., include a surrounding area of particular size, which may be predefined and/or adjusted by the operator). To further enhance the detection (e.g., increase its reliability), multiple ones of the projection-based 2D images (e.g., preferably all of them) may be processed in the same manner, and then the identified abnormalities may be compared to validate the detection results. This is further illustrated in FIGS. 5A, 5B, 6, and 7.

Figure 5A:
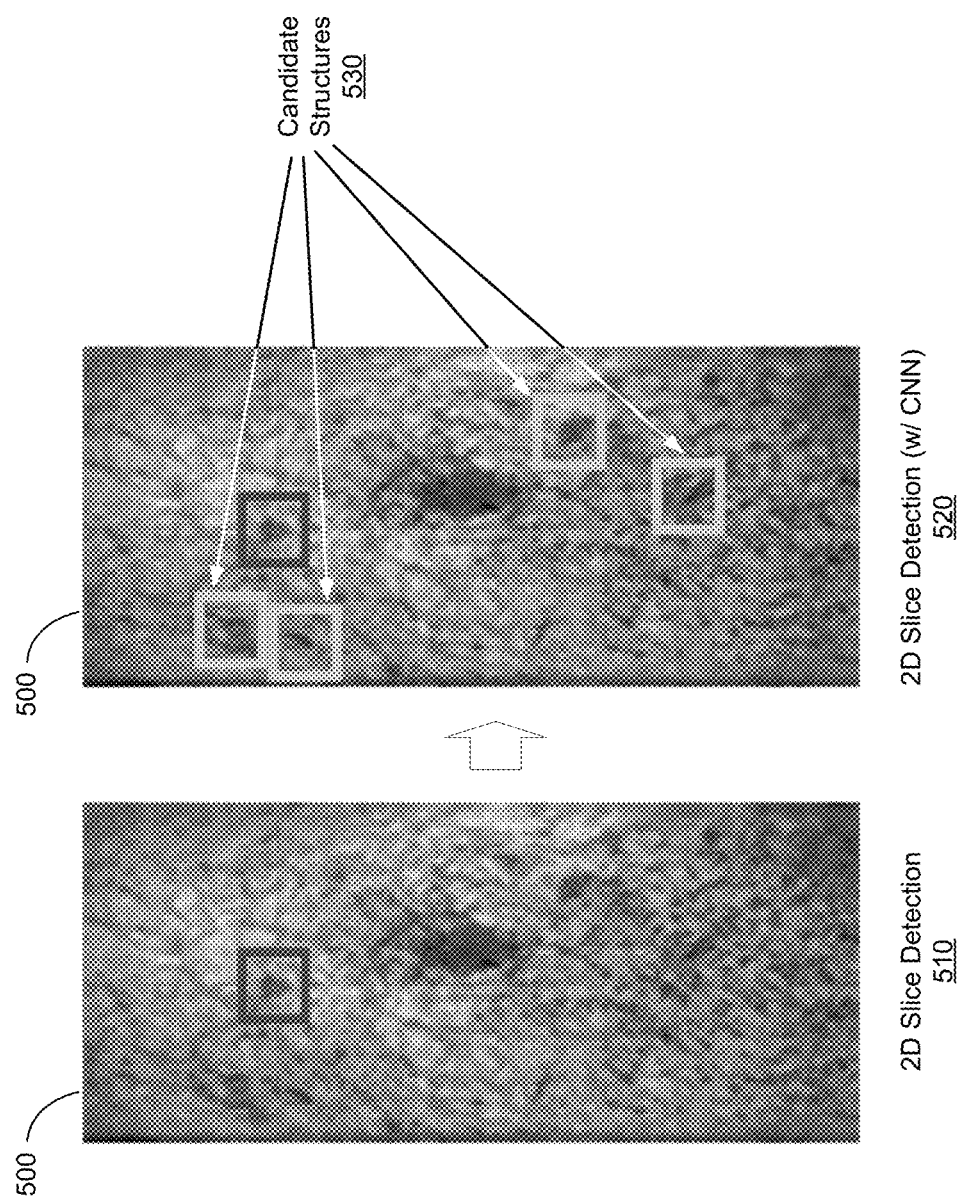
FIGS. 5A and 5B illustrate an example processing of a coronal projection of automated breast ultrasound screening (ABUS) volume, in accordance with the present disclosure.
Figure 5B:
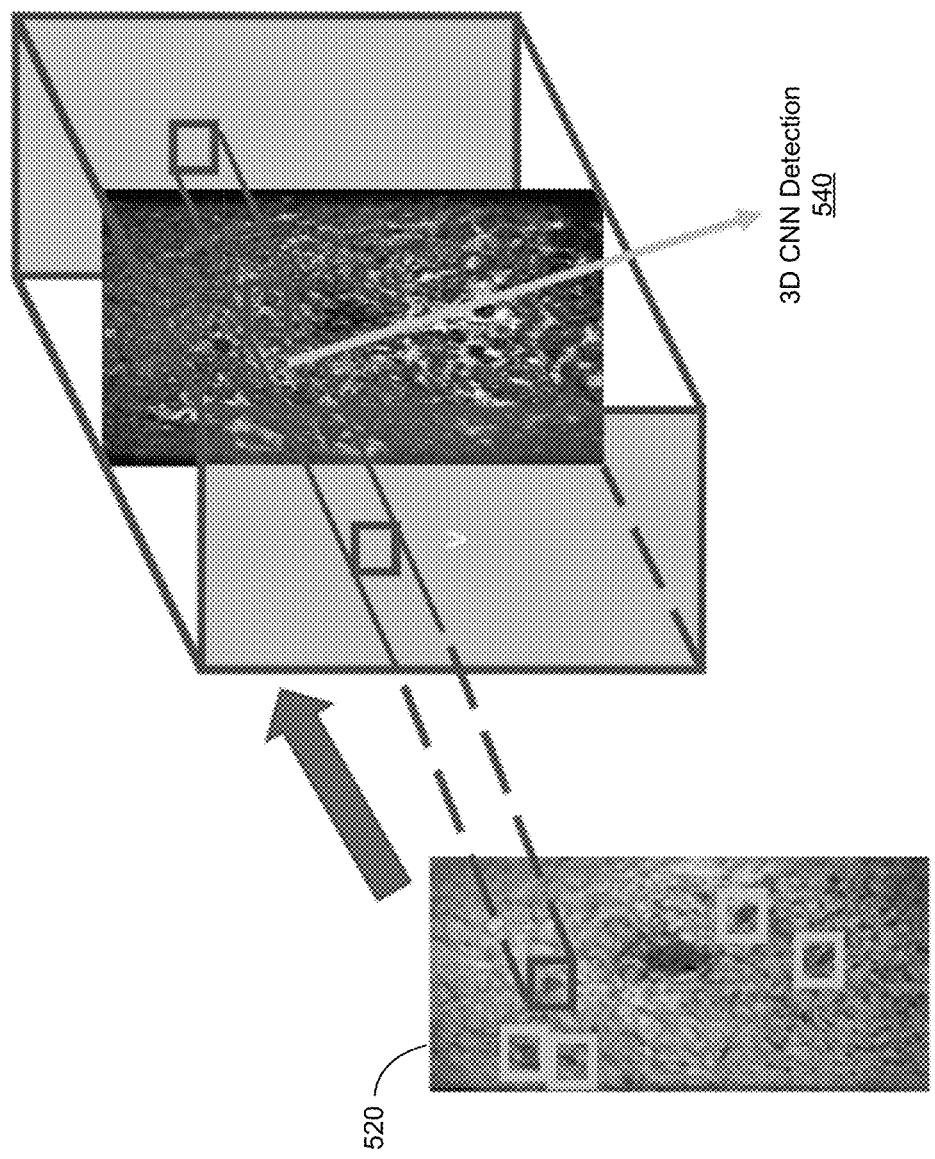

FIGS. 5A and 5B illustrate an example processing of a coronal projection of automated breast ultrasound screening (ABUS) volume, in accordance with the present disclosure. Shown in FIGS. 5A and 5B is a two-dimensional (2D) image 500 corresponding to a projection of an ABUS volume in a particular direction. For example, the 2D image 500 may represent a 2D image corresponding to a coronal projection of an ABUS volume. Thus, the 2D image 500 may correspond to, for example, the coronal 2D image 420 of FIG. 4.

As shown in FIG. 5A, the 2D image 500 may be processed for abnormalities (e.g., lesions) detection. In this regard, the 2D image 500 initially (510) may be subjected to basic lesion detection, which may allow for detecting clear lesions—that is, structures that meet some particular criteria for "certain" lesions—e.g., the lesions appearing darker than their surroundings, such as based on preset darkness threshold(s) (e.g., absolute or relative to surrounding tissue).

Next, a more adaptive detection may be applied (520) to detect candidate lesions. For example, a two-dimensional (2D) convolutional neural network (CNN) based detection may then be applied to the 2D image 500, with high sensitivity being used, e.g., to detect lesion candidates 530 in the image. In other words, the 2D CNN based detection may be employed to detect lesion-like structures, which may correspond to lesion candidates.

Next, three-dimensional (3D) detection is then applied, being limited to only the identified lesion candidates, and only in the direction of projection used to generated the 2D image, as illustrated in FIG. 5B. In other words, after the candidate detection step (520), in which the lesion candidates 530 are detected and identified based on the 2D detection (e.g., using enhanced 2D detection, such as 2D CNN based detection), the 3D search for potential lesions would be limited to only those candidates, and only in the coronal direction (or y-direction) in the ABUS volume.

In this regard, three-dimensional (3D) convolutional neural network (CNN) detection may be used in the coronal path of projection, with a volume of interest (VoI) selected for each candidate in original the ABUS volume. The 3D CNN based lesion detection may be performed at full spatial resolution, as it is limited to small volume(s)—that is, the selected volumes of interest (VoIs) rather than the whole ABUS volume.

Thus, as shown in FIG. 5B, for each of the lesion candidates 530, a 3D CNN is employed on 3D patches in the projection direction (coronal in this case) within the original ABUS volume, to detect accurately the presence of lesions. Accordingly, the computationally expensive 3D CNN can be run on the ABUS volume at full image (e.g., spatial) resolution in a local neighborhood improving the detection performance (especially for smaller lesions).

Figure 6:
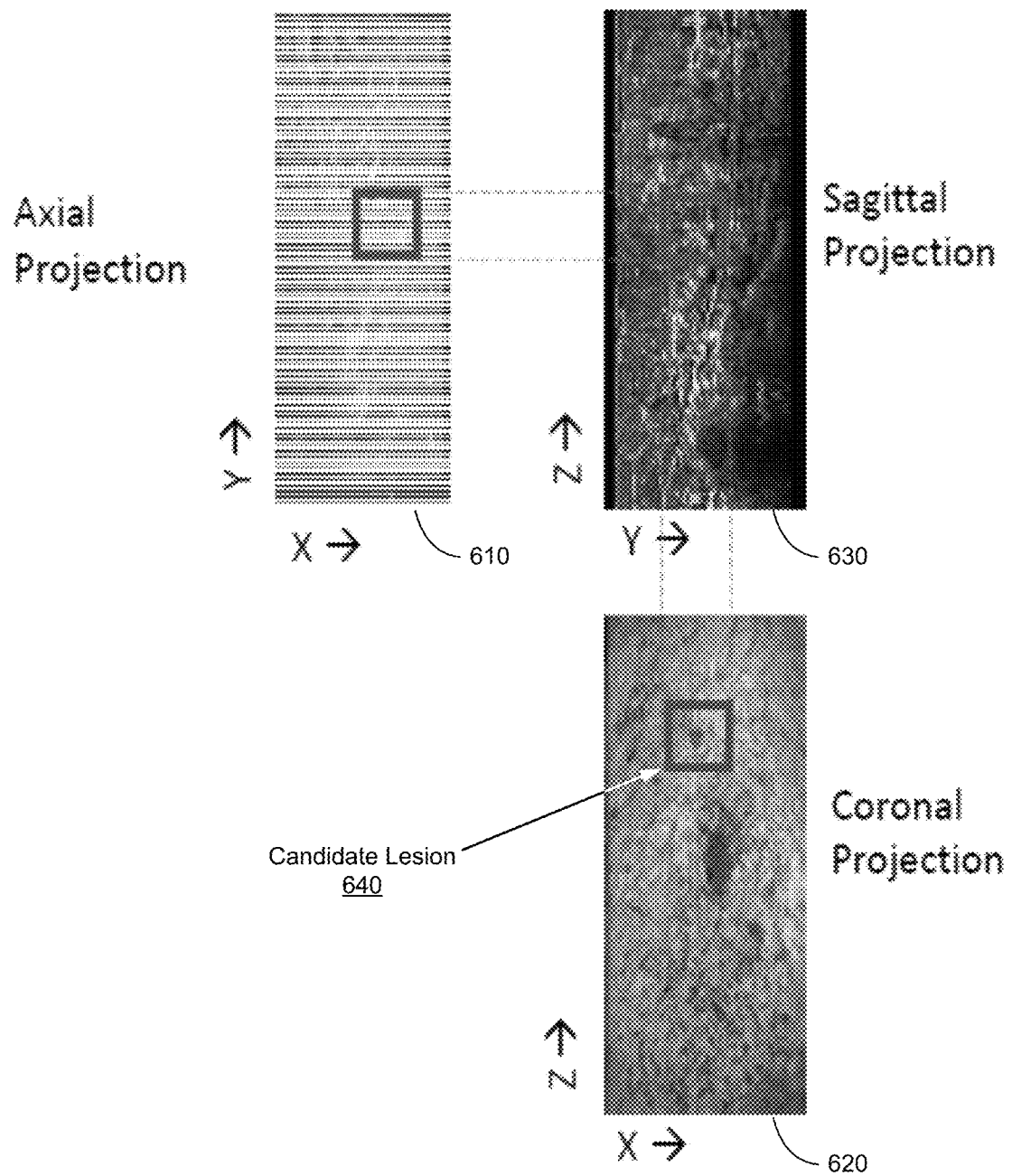
FIG. 6 illustrates an example lesion reinforcement using multiple projections of automated breast ultrasound screening (ABUS) volume, in accordance with the present disclosure.

FIG. 6 illustrates an example lesion reinforcement using multiple projections of automated breast ultrasound screening (ABUS) volume, in accordance with the present disclosure. Shown in FIG. 6 are two-dimensional (2D) images 610, 620, and 630 corresponding, respectively, to axial projection, coronal projection, and sagittal projection of an ultrasound volume (e.g., the ABUS volume 300 of FIG. 3).

As illustrated in FIG. 6, the multiple projections, and 2D images generated based thereon, may be used for lesion reinforcement—that is, to validate identified candidate lesions. For example, as shown in FIG. 6, a lesion candidate 640 may be detected in the coronal projection/2D image 620, such as based on detection process as described with respect to FIGS. 5A and 5B. To validate the candidate lesions (e.g., the candidate lesion 640), one or both of the remaining projections/2D images may also be subjected to the lesion detection process in the same manner.

The projections/2D images in the three axis aligned directions may then be compared, to validate the detected lesions. In this regard, real lesions should reinforce each other—e.g., match spatially within the different projections/ 2D images, as shown in FIG. 6. On the other hand, candidates that are not reinforced—that is, candidates detected in one projection/2D image are not reinforced by one or both of the other projections/2D images—may be designated as false positives, and may be discarded.

Figure 7:
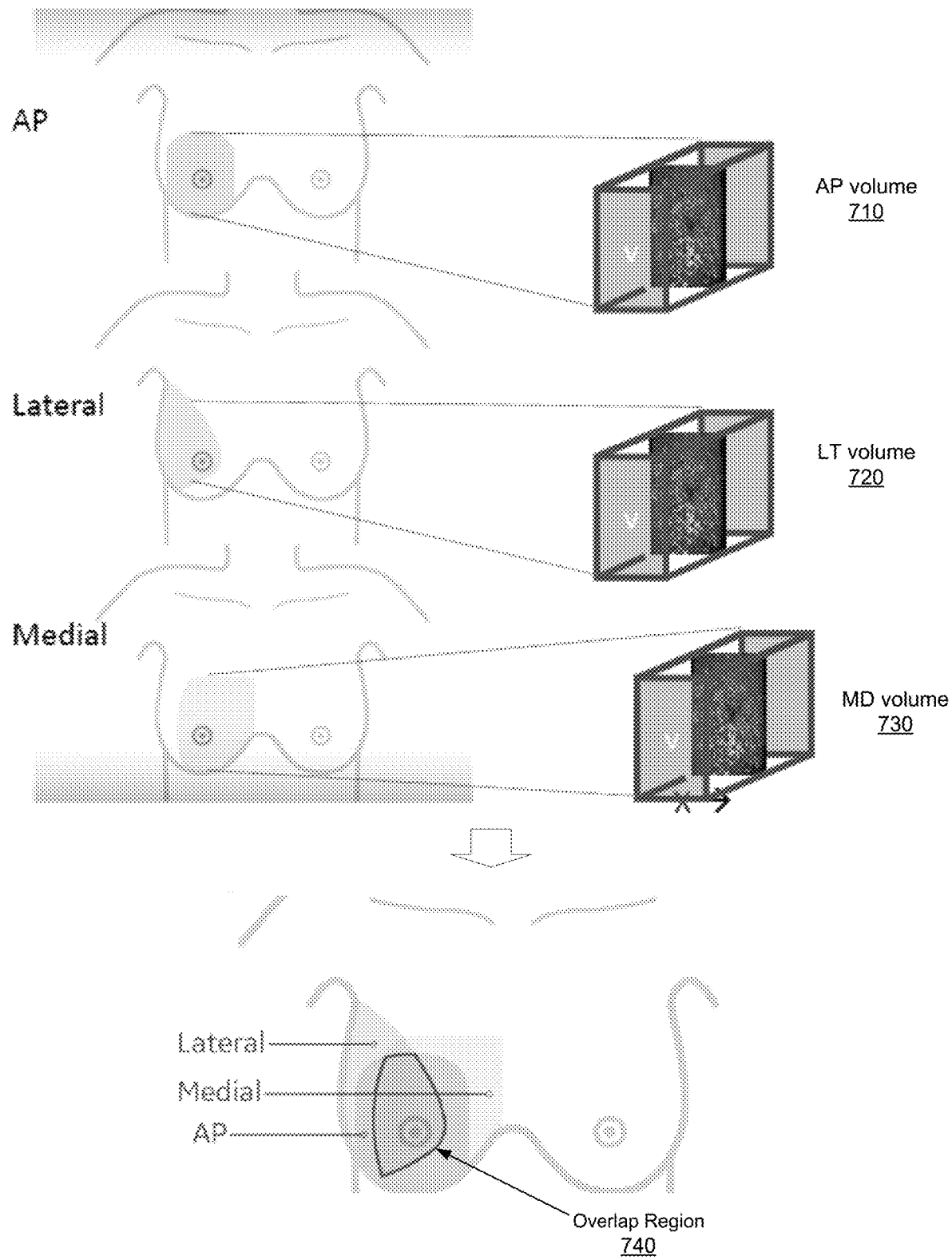
FIG. 7 illustrates an example lesion reinforcement using multiple automated breast ultrasound screening (ABUS) volumes, in accordance with the present disclosure.

FIG. 7 illustrates an example lesion reinforcement using multiple automated breast ultrasound screening (ABUS) volumes, in accordance with the present disclosure. Shown in FIG. 7 are Anteroposterior (AP), Medial and Lateral volumes 710, 720, and 730.

The Anteroposterior (AP), Medial and Lateral volumes 710, 720, and 730 may be generated and processed using an ultrasound system, such as the ultrasound system 200 of FIG. 2. In this regard, the Anteroposterior (AP), Medial and Lateral volumes 710, 720, and 730 may comprise ABUS volumes—that is, may be generated during an ABUS scan—covering the Anteroposterior (AP), Medial and Lateral sections of a scanned breast.

As illustrated in FIG. 7, the multiple volumes may be used for lesion reinforcement—that is, to validate identified candidate lesions, particularly lesion candidates located within an overlapped region 740 of all three volumes. For example, after applying lesion detection process to each of the volumes 710, 720, and 730, as described above (e.g., with respect to FIGS. 3-6), detected candidates may be validated using all three volumes.

In this regard, the sections of the volumes 710, 720, and 730 that are within the overlapped region 740 be compared, to validate the detected lesions therein. In this regard, real lesions should reinforce each other—e.g., match spatially within the different volumes. On the other hand, candidates that are not reinforced—that is, candidates detected in one volume that are not reinforced by one or both of the other volumes—may be designated as false positives, and may be discarded.

Figure 8:
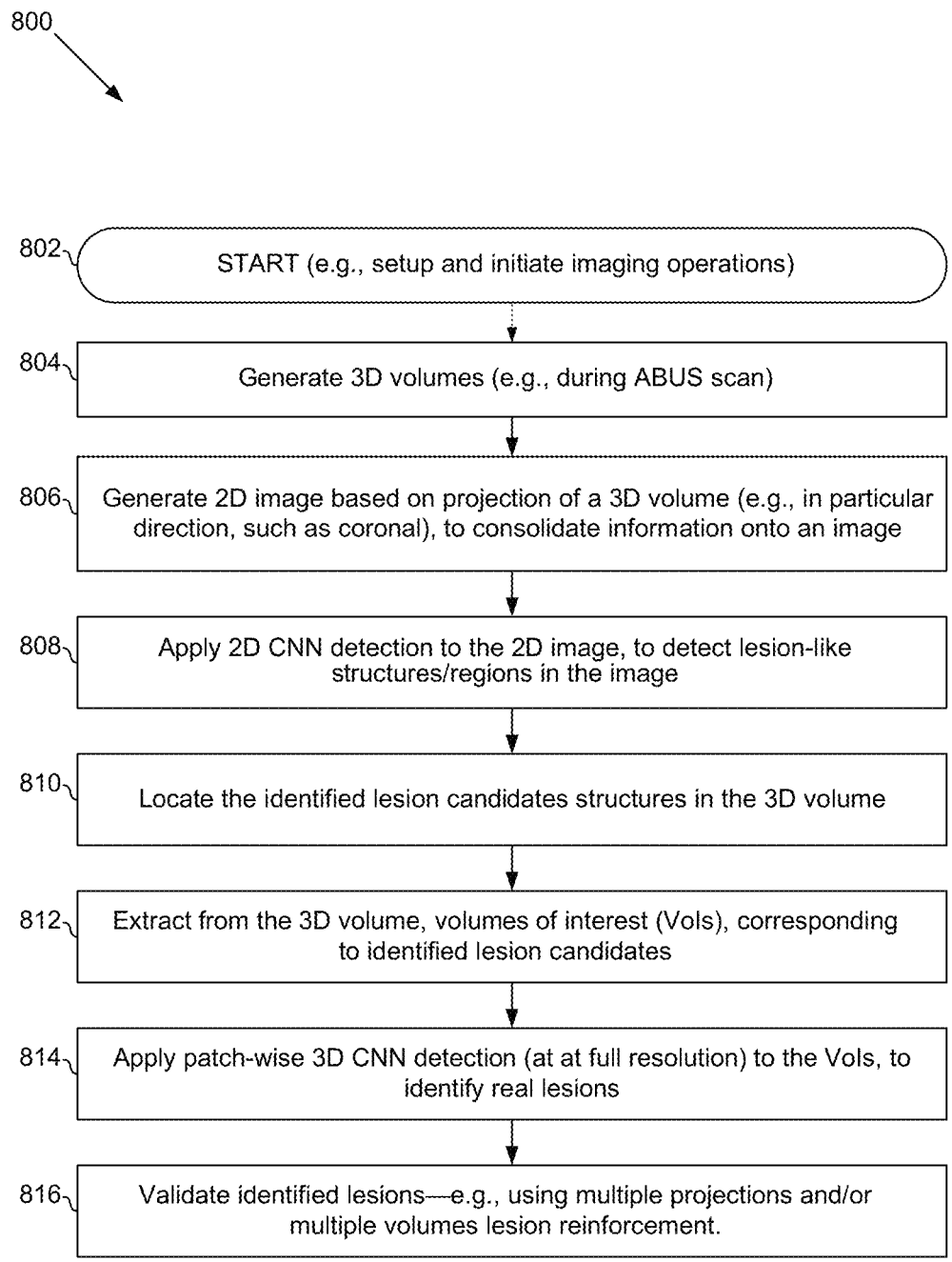
FIG. 8 illustrates a flowchart of an example process for projection profile enabled computer aided detection (CAD) based processing of automated breast ultrasound screening (ABUS) volume, in accordance with the present disclosure.

FIG. 8 illustrates a flowchart of an example process for projection profile enabled computer aided detection (CAD) based processing of automated breast ultrasound screening (ABUS) volume, in accordance with the present disclosure.

Shown in FIG. 8 is flow chart 800, comprising a plurality of example steps (represented as blocks 802-816), which may be performed in a suitable system (e.g., system 200 of FIG. 2) for performing projection profile enabled computer aided detection (CAD).

In start step 802, the system may be setup, and operations may initiate.

In step 804, three-dimensional (3D) ultrasound volumes may be generated (e.g., during ABUS scan).

In step 806, two-dimensional (2D) image(s) may be generated based on projection of a particular 3D volume (e.g., in particular direction, such as coronal), to consolidate information onto an image.

In step 808, two-dimensional (2D) convolutional neural network (CNN) detection may be applied to the 2D image, to detect lesion-like structures/regions in the image.

In step 810, the identified lesion candidates structures may be located (e.g., spatial information corresponding thereto) within the 3D volume.

In step 812, volumes of interest (VoIs), corresponding to the identified lesion candidates structures, may be extracted from the 3D volume.

In step 814, three-dimensional (3D) convolutional neural network (CNN) detection may be applied patch-wise, at full resolution, to the extracted VoIs, to identify real lesions.

In step 816, Validate identified lesions—e.g., using multiple projections and/or multiple volumes lesion reinforcement.

An example system for ultrasound imaging in accordance with the present disclosure comprises an ultrasound device comprising at least one processor, the ultrasound device being configured to generate volumetric ultrasound dataset, based on echo ultrasound signals; generate based on the volumetric ultrasound dataset, a three-dimensional (3D) ultrasound volume; and apply selective structure detection to the three-dimensional (3D) ultrasound volume. The selective structure detection comprises generating based on a projection of the three-dimensional (3D) ultrasound volume in a particular spatial direction, a two-dimensional (2D) image; applying two-dimensional (2D) structure detection to the two-dimensional (2D) image, wherein the two-dimensional (2D) structure detection is configured to identify structure candidates associated with a particular type of structures, the particular type of structures comprising abnormal tissue structures in a particular body part; selecting for each identified structure candidate, a corresponding local volume within the three-dimensional (3D) ultrasound volume; applying three-dimensional (3D) structure detection to each selected local volume; and identifying based on applying the three-dimensional (3D) structure detection, one or more structure candidates that match the particular type of structures. The three-dimensional (3D) structure detection is configured to compare characteristics associated with the structure candidate with the particular type of structures, and the three-dimensional (3D) structure detection is applied at full-resolution to each selected local volume.

In an example implementation, the ultrasound device is configured to apply the selective structure detection based on a projection of the three-dimensional (3D) ultrasound volume in at least one other spatial direction.

In an example implementation, the ultrasound device is configured to validate one or more identified structure candidates that match the particular type of structures based on the selective structure detection corresponding to the projection of the three-dimensional (3D) ultrasound volume in the at least one other spatial direction.

In an example implementation, the ultrasound device is configured to validate each of the one or more identified structure candidates based on spatial matching with a corresponding identified structure candidate determined based on the selective structure detection corresponding to the projection of the three-dimensional (3D) ultrasound volume in the at least one other spatial direction.

In an example implementation, the ultrasound device is configured to generate based on the volumetric ultrasound dataset, at least one other three-dimensional (3D) ultrasound volume; and apply the selective structure detection to the at least one other three-dimensional (3D) ultrasound volume.

In an example implementation, the ultrasound device is configured to determine an overlapping region between the three-dimensional (3D) ultrasound volume and the at least one other three-dimensional (3D) ultrasound volume; and validate one or more identified structure candidates that match the particular type of structures, that are located with the overlapping region, based on the selective structure detection applied to the at least one other three-dimensional (3D) ultrasound volume.

In an example implementation, the ultrasound device is configured to validate each of the one or more identified structure candidates based on spatial matching with a corresponding identified structure candidate, that is within the overlapping region, determined based on the selective structure detection corresponding to the projection of the three-dimensional (3D) ultrasound volume in the at least one other spatial direction.

In an example implementation, the ultrasound device is configured to adjust the two-dimensional (2D) structure detection based on an adaptive learning algorithm.

In an example implementation, the ultrasound device is configured to adjust the three-dimensional (3D) structure detection based on an adaptive learning algorithm.

An example method for ultrasound imaging in accordance with the present disclosure comprises generating volumetric ultrasound dataset, based on echo ultrasound signals; generating based on the volumetric ultrasound dataset, a three-dimensional (3D) ultrasound volume; and applying selective structure detection to the three-dimensional (3D) ultrasound volume. The selective structure detection comprising: generating based on a projection of the three-dimensional (3D) ultrasound volume in a particular spatial direction, a two-dimensional (2D) image; applying two-dimensional (2D) structure detection to the two-dimensional (2D) image, wherein the two-dimensional (2D) structure detection is configured to identify structure candidates associated with a particular type of structures, the particular type of structures comprising abnormal tissue structures in a particular body part; selecting for each identified structure candidate, a corresponding local volume within the three-dimensional (3D) ultrasound volume; applying three-dimensional (3D) structure detection to each selected local volume; and identifying based on applying the three-dimensional (3D) structure detection, one or more structure candidates that match the particular type of structures. The three-dimensional (3D) structure detection is configured to compare characteristics associated with the structure candidate with the particular type of structures, and the three-dimensional (3D) structure detection is applied at full-resolution to each selected local volume.

In an example implementation, the method further comprises applying the selective structure detection based on a projection of the three-dimensional (3D) ultrasound volume in at least one other spatial direction.

In an example implementation, the method further comprises validating one or more identified structure candidates that match the particular type of structures based on the selective structure detection corresponding to the projection of the three-dimensional (3D) ultrasound volume in the at least one other spatial direction.

In an example implementation, the method further comprises validating each of the one or more identified structure candidates based on spatial matching with a corresponding identified structure candidate determined based on the selective structure detection corresponding to the projection of the three-dimensional (3D) ultrasound volume in the at least one other spatial direction.

In an example implementation, the method further comprises generating based on the volumetric ultrasound dataset, at least one other three-dimensional (3D) ultrasound volume; and applying the selective structure detection to the at least one other three-dimensional (3D) ultrasound volume.

In an example implementation, the method further comprises determine an overlapping region between the three-dimensional (3D) ultrasound volume and the at least one other three-dimensional (3D) ultrasound volume; and validate one or more identified structure candidates that match the particular type of structures, that are located with the overlapping region, based on the selective structure detection applied to the at least one other three-dimensional (3D) ultrasound volume.

In an example implementation, the method further comprises validating each of the one or more identified structure candidates based on spatial matching with a corresponding identified structure candidate, that is within the overlapping region, determined based on the selective structure detection corresponding to the projection of the three-dimensional (3D) ultrasound volume in the at least one other spatial direction.

In an example implementation, the method further comprises adjusting the two-dimensional (2D) structure detection based on an adaptive learning algorithm.

In an example implementation, the method further comprises adjusting the three-dimensional (3D) structure detection based on an adaptive learning algorithm.

In an example implementation, the two-dimensional (2D) structure detection further comprises convolutional neural network (CNN) based detection.

In an example implementation, the three-dimensional (3D) structure detection further comprises convolutional neural network (CNN) based detection.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system, comprising:
an ultrasound device, comprising at least one processor, wherein the ultrasound device is configured to:
generate volumetric ultrasound dataset, based on echo ultrasound signals;
generate based on the volumetric ultrasound dataset, a three-dimensional (3D) ultrasound volume; and
apply selective structure detection to the three-dimensional (3D) ultrasound volume, the selective structure detection comprising:
generating based on a projection of the three-dimensional (3D) ultrasound volume in a particular spatial direction, a two-dimensional (2D) image;
applying two-dimensional (2D) structure detection to the two-dimensional (2D) image, wherein the two-dimensional (2D) structure detection is configured to identify structure candidates associated with a particular type of structures, the particular type of structures comprising abnormal tissue structures in a particular body part;
selecting for each identified structure candidate, a corresponding local volume within the three-dimensional (3D) ultrasound volume;
applying three-dimensional (3D) structure detection to each selected local volume, wherein:
the three-dimensional (3D) structure detection is configured to compare characteristics associated with the structure candidate with the particular type of structures, and
the three-dimensional (3D) structure detection is applied at full-resolution to each selected local volume; and
identifying based on applying the three-dimensional (3D) structure detection, one or more structure candidates that match the particular type of structures.

2. The system of claim 1, wherein the ultrasound device is configured to apply the selective structure detection based on a projection of the three-dimensional (3D) ultrasound volume in at least one other spatial direction.

3. The system of claim 2, wherein the ultrasound device is configured to validate one or more identified structure candidates that match the particular type of structures based on the selective structure detection corresponding to the projection of the three-dimensional (3D) ultrasound volume in the at least one other spatial direction.

4. The system of claim 3, wherein the ultrasound device is configured to validate each of the one or more identified structure candidates based on spatial matching with a corresponding identified structure candidate determined based on the selective structure detection corresponding to the projection of the three-dimensional (3D) ultrasound volume in the at least one other spatial direction.

5. The system of claim 1, wherein the ultrasound device is configured to:
generate based on the volumetric ultrasound dataset, at least one other three-dimensional (3D) ultrasound volume; and
apply the selective structure detection to the at least one other three-dimensional (3D) ultrasound volume.

6. The system of claim 5, wherein the ultrasound device is configured to:
determine an overlapping region between the three-dimensional (3D) ultrasound volume and the at least one other three-dimensional (3D) ultrasound volume; and
validate one or more identified structure candidates that match the particular type of structures, that are located with the overlapping region, based on the selective structure detection applied to the at least one other three-dimensional (3D) ultrasound volume.

7. The system of claim 6, wherein the ultrasound device is configured to validate each of the one or more identified structure candidates based on spatial matching with a corresponding identified structure candidate, that is within the overlapping region, determined based on the selective structure detection corresponding to the projection of the three-dimensional (3D) ultrasound volume in the at least one other spatial direction.

8. The system of claim 1, wherein the ultrasound device is configured to adjust the two-dimensional (2D) structure detection based on an adaptive learning algorithm.

9. The system of claim 1, wherein the ultrasound device is configured to adjust the three-dimensional (3D) structure detection based on an adaptive learning algorithm.

10. A method, comprising:
generating volumetric ultrasound dataset, based on echo ultrasound signals;
generating based on the volumetric ultrasound dataset, a three-dimensional (3D) ultrasound volume; and
applying selective structure detection to the three-dimensional (3D) ultrasound volume, the selective structure detection comprising:
generating based on a projection of the three-dimensional (3D) ultrasound volume in a particular spatial direction, a two-dimensional (2D) image;
applying two-dimensional (2D) structure detection to the two-dimensional (2D) image, wherein the two-dimensional (2D) structure detection is configured to identify structure candidates associated with a particular type of structures, the particular type of structures comprising abnormal tissue structures in a particular body part;
selecting for each identified structure candidate, a corresponding local volume within the three-dimensional (3D) ultrasound volume;
applying three-dimensional (3D) structure detection to each selected local volume, wherein:
the three-dimensional (3D) structure detection is configured to compare characteristics associated with the structure candidate with the particular type of structures, and
the three-dimensional (3D) structure detection is applied at full-resolution to each selected local volume; and
identifying based on applying the three-dimensional (3D) structure detection, one or more structure candidates that match the particular type of structures.

11. The method of claim 10, comprising applying the selective structure detection based on a projection of the three-dimensional (3D) ultrasound volume in at least one other spatial direction.

12. The method of claim 11, comprising validating one or more identified structure candidates that match the particular type of structures based on the selective structure detection corresponding to the projection of the three-dimensional (3D) ultrasound volume in the at least one other spatial direction.

13. The method of claim 12, comprising validating each of the one or more identified structure candidates based on spatial matching with a corresponding identified structure candidate determined based on the selective structure detection corresponding to the projection of the three-dimensional (3D) ultrasound volume in the at least one other spatial direction.

14. The method of claim 10, comprising:
generating based on the volumetric ultrasound dataset, at least one other three-dimensional (3D) ultrasound volume; and
applying the selective structure detection to the at least one other three-dimensional (3D) ultrasound volume.

15. The method of claim 14, comprising:
determine an overlapping region between the three-dimensional (3D) ultrasound volume and the at least one other three-dimensional (3D) ultrasound volume; and
validate one or more identified structure candidates that match the particular type of structures, that are located with the overlapping region, based on the selective structure detection applied to the at least one other three-dimensional (3D) ultrasound volume.

16. The method of claim 15, comprising validating each of the one or more identified structure candidates based on spatial matching with a corresponding identified structure candidate, that is within the overlapping region, determined based on the selective structure detection corresponding to the projection of the three-dimensional (3D) ultrasound volume in the at least one other spatial direction.

17. The method of claim 10, comprising adjusting the two-dimensional (2D) structure detection based on an adaptive learning algorithm.

18. The method of claim 10, comprising adjusting the three-dimensional (3D) structure detection based on an adaptive learning algorithm.

19. The method of claim 10, wherein the two-dimensional (2D) structure detection comprises convolutional neural network (CNN) based detection.

20. The method of claim 10, wherein the three-dimensional (3D) structure detection comprises convolutional neural network (CNN) based detection.

* * * * *